United States Patent

Ornitz

[11] Patent Number: 6,051,547
[45] Date of Patent: Apr. 18, 2000

[54] SCENTED JEWELRY

[76] Inventor: Kim Ornitz, 1026 N. Croft Ave., Los Angeles, Calif. 90069

[21] Appl. No.: 09/270,276

[22] Filed: Mar. 16, 1999

[51] Int. Cl.[7] ...................................... A61K 7/46
[52] U.S. Cl. ............................ 512/1; 63/DIG. 2; 428/905
[58] Field of Search ........................ 63/DIG. 2; 428/905; 512/1

[56] References Cited

U.S. PATENT DOCUMENTS

| | | | |
|---|---|---|---|
| 4,293,602 | 10/1981 | Coffey et al. | 428/28 |
| 4,356,115 | 10/1982 | Shibanai et al. | 252/522 A |
| 4,499,012 | 2/1985 | Farrell | 252/522 A |
| 4,874,129 | 10/1989 | DiSapio et al. | 239/36 |
| 4,950,542 | 8/1990 | Barker | 428/403 |
| 5,041,421 | 8/1991 | King | 512/4 |

FOREIGN PATENT DOCUMENTS 650144  7/1844  France .

*Primary Examiner*—Gabrielle Brouillette
*Assistant Examiner*—Monique Cole
*Attorney, Agent, or Firm*—Rob L. Phillips

[57] ABSTRACT

A flexible, durable and pleasant smelling article of jewelry is disclosed which consists of a combination of essential oils and raw silicon that is molded under specific temperatures and pressures. A method for molding the article of jewelry is also disclosed.

3 Claims, No Drawings

SCENTED JEWELRY

FIELD OF THE INVENTION

The present invention relates to a method for producing fragrance emitting jewelry. Silicon is integrated with essential oils and thereafter formed into items to be worn as jewelry. The use of silicon is very effective in emitting the chosen fragrance over a long period of time and is also flexible and strong enough to endure the wear and tear encountered by everyday jewelry.

BACKGROUND OF THE INVENTION

Aroma emitting articles and methods of producing the same are disclosed throughout the prior art. The prior art further discloses jewelry that emits a pleasant fragrance by several different means. A thorough examination of the prior art reveals that the method and resultant product disclosed in this application are both unique and nonobvious in their simplicity and overall integration of fragrance and silicon.

U.S. Pat. No. 4,293,602 discloses jewelry formed from natural botanical materials. The patent shows that flowers, roots, herbs and essential oils are bonded with a fluorocarbon resin to form specific pieces of jewelry. The present invention is much simpler to create since it uses only silicon and essential oils rather than natural botanical materials which can be difficult to work with. Furthermore, the present invention uses silicon which results in jewelry that is more flexible as well as more durable than that disclosed in U.S. Pat. No. 4,293,602.

U.S. Pat. Nos. 4,356,115, 4,499,012 and U.S. Pat. No. 5,041,421 disclose dry-pulverized cyclodextin, vermiculite and sodium chloride granules as their fragrance carrier respectively. None of the patents suggest the use of silicon as a fragrance carrying medium nor do they suggest using the resultant substance as jewelry.

A unique method of coating existing articles with fragrances is disclosed in U.S. Pat. No. 4,950,542. The patent reveals a method of coating costume jewelry and other items with an aroma emitting film. The present invention differs in that the fragrance is integrated with the silicon rather than simply a film that covers the silicon.

Yet another invention disclosed in French patent 650,144 reveals jewelry which is capable of encapsulating perfume in liquid or solid form. The articles of jewelry are designed with a compartment that can be filled with either liquid or solid perfume. Thereafter the fragrance is released until such time that the perfume evaporates or loses its aroma. This jewelry is limited in that it requires valuable space able to contain the perfume. Therefore, the jewel, will in most instances be too large or gaudy to be worn under normal circumstances.

The present invention solves the shortcomings of the prior art by integrating essential oils with silicon which is ultimately molded to form flexible, durable and pleasant smelling articles of jewelry.

SUMMARY OF THE INVENTION

Accordingly, the present novel invention discloses a method of integrating essential oils with silicon into a compound that is molded into articles of jewelry.

The essential oils are integrated with the silicon which effectively releases the aroma of the essential oils over a long period of time. The silicon not only performs well as a fragrance carrier, but it is also very flexible, strong and durable allowing it to be molded into various long-lasting articles of jewelry.

The novel use of silicon and novel approach utilized to combine the essential oils and silicon maximizes the effectiveness of the fragrance emitting jewelry.

Other objects, features and advantages of the invention will be readily apparent from the following description of certain preferred embodiments. It is understood that modifications and variations may be effectuated without departing from the spirit and scope of the present invention.

Producing the fragrance emitting jewelry is accomplished by combining essential oils with silicon and molding the resultant combination under pressure and temperature parameters. Essential oils work well because they are easily integrated with the silicon and have a strong aroma that is retained over a long period of time by the silicon.

The essential oils are combined with raw silicon by the use of a rubber mill. The use of a rubber mill is the preferred machine utilized to effectuate this combination, however, other instrumentality may be utilized to accomplish a similar desired result. A desired quantity of the resultant mixture of essential oils and silicon is placed in a mold a subjected to temperatures in the range of 330° F. to 370° F. and pressures in the range of 2200 lb/in$^2$ to 2400 lb/in$^2$ for approximately 4 minutes. This curing process results in a flexible, durable and pleasant smelling substance capable of being worn as jewelry.

The preferred mold utilized is designed to result in ring-like silicon piece that can be worn as a ring, bracelet or necklace depending on the diameter of the void encapsulated by the mold. Other items of jewelry are possible but those disclosed herein are the preferred articles of jewelry to be produced by the disclosed method.

What is claimed is:

1. A method of producing a fragrance emitting article of jewelry comprising the steps of:
   a) a means for combining essential oils with raw silicon;
   b) placing a combination of essential oils and raw silicon in a mold corresponding to a desired article of jewelry;
   c) subjecting said combination of essential oils and raw silicon to temperatures between 330° F. and 370° F. and pressures between 2200 lb/in$^2$ and 2400 lb/in$^2$ for approximately 4 minutes.

2. A method according to claim 1 wherein the means for combining said essential oils with said raw silicon is a rubber mill.

3. Jewelry produced in accordance with the method of claim 1.

* * * * *